(12) United States Patent
Knape et al.

(10) Patent No.: US 10,314,598 B2
(45) Date of Patent: Jun. 11, 2019

(54) DRILL GUIDE

(71) Applicant: Stryker European Holdings I, LLC, Kalamazoo, MI (US)

(72) Inventors: Martin Knape, March-Hugstetter (DE); Denis Digeser, Freiburg (DE); Cem Adalioglu, Mönkeberg (DE); Frank Rothmann, Laupheim (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 534 days.

(21) Appl. No.: 15/139,819

(22) Filed: Apr. 27, 2016

(65) Prior Publication Data
US 2016/0235419 A1 Aug. 18, 2016

Related U.S. Application Data

(62) Division of application No. 13/545,377, filed on Jul. 10, 2012, now Pat. No. 9,572,589.

(51) Int. Cl.
*A61B 17/16* (2006.01)
*A61B 17/17* (2006.01)
*A61B 90/00* (2016.01)

(52) U.S. Cl.
CPC .......... *A61B 17/17* (2013.01); *A61B 17/1615* (2013.01); *A61B 17/1633* (2013.01); *A61B 2090/034* (2016.02); *A61B 2090/062* (2016.02)

(58) Field of Classification Search
None
See application file for complete search history.

(56) References Cited

U.S. PATENT DOCUMENTS

| | | |
|---|---|---|
| 412,952 A | 10/1889 | Elterich |
| 2,243,718 A | 5/1941 | Moreira |
| 2,294,303 A | 8/1942 | Jagow |
| 2,526,662 A | 10/1950 | Hipps et al. |
| 3,112,743 A | 12/1963 | Cochran et al. |
| 3,128,768 A | 4/1964 | Geistauts |
| 4,273,117 A | 6/1981 | Neuhauser |

(Continued)

FOREIGN PATENT DOCUMENTS

| | | |
|---|---|---|
| DE | 102009033138 A1 | 2/2011 |
| EP | 1374784 A1 | 1/2004 |
| EP | 2013/064512 | 10/2013 |

OTHER PUBLICATIONS

International Search Report for Application No. PCT/EP2013/064512 dated Oct. 10, 2013.

*Primary Examiner* — Samuel S Hanna
(74) *Attorney, Agent, or Firm* — Lerner, David, Littenberg, Krumholz & Mentlik, LLP (57) ABSTRACT

A drill guide for drilling bone comprising a housing having a bore running through the housing is disclosed. In one embodiment, the drill guide may comprise a locking member coupled to the housing that is adapted to engage with a locking portion of a drill bit to lock the drill bit axially within the housing. The locking member may also be adapted to disengage with the drill bit to allow the drill bit to move within the bore of the housing and be inserted into bone. A movable guide may also be provided with the drill guide, such movable guide including a bore for receiving a portion of the drill bit and allowing the same to move axially within the housing. Methods of using the aforementioned drill guide are also disclosed.

13 Claims, 5 Drawing Sheets

(56) References Cited

U.S. PATENT DOCUMENTS

| | | |
|---|---|---|
| 4,341,206 A | 7/1982 | Perrett et al. |
| 4,399,813 A | 8/1983 | Barber |
| 4,710,075 A | 12/1987 | Davison |
| 4,954,025 A | 9/1990 | Crawford et al. |
| 4,969,781 A | 11/1990 | Fahrner et al. |
| 5,013,318 A | 5/1991 | Spranza, III |
| 5,051,043 A | 9/1991 | Spitznagel |
| 5,112,335 A | 5/1992 | Laboureau et al. |
| 5,122,146 A | 6/1992 | Chapman et al. |
| 5,133,720 A | 7/1992 | Greenberg |
| 5,180,388 A | 1/1993 | Dicarlo |
| 5,300,077 A | 4/1994 | Howell |
| 5,409,490 A | 4/1995 | Ethridge |
| 5,409,493 A | 4/1995 | Greenberg |
| 5,507,801 A | 4/1996 | Gisin |
| 5,536,271 A | 7/1996 | Daly et al. |
| 5,570,706 A | 11/1996 | Howell |
| 5,575,794 A | 11/1996 | Walus et al. |
| 5,595,193 A | 1/1997 | Walus et al. |
| 5,667,509 A | 9/1997 | Westin |
| 5,746,743 A | 5/1998 | Greenberg |
| 5,810,828 A | 9/1998 | Lightman et al. |
| 5,895,389 A | 4/1999 | Schenk et al. |
| 5,951,561 A | 9/1999 | Pepper et al. |
| 6,019,767 A | 2/2000 | Howell |
| 6,063,088 A * | 5/2000 | Winslow .............. A61B 17/025 606/279 |
| 6,110,178 A | 8/2000 | Zech et al. |
| 6,146,385 A | 11/2000 | Torrie et al. |
| 6,159,214 A | 12/2000 | Michelson |
| 6,254,604 B1 | 7/2001 | Howell |
| 6,254,605 B1 | 7/2001 | Howell |
| 6,277,121 B1 | 8/2001 | Burkinshaw et al. |
| 6,358,253 B1 | 3/2002 | Torrie et al. |
| 6,436,098 B1 | 8/2002 | Michelson |
| 6,547,795 B2 | 4/2003 | Schneiderman |
| 6,635,062 B2 | 10/2003 | Ray et al. |
| 6,699,253 B2 | 3/2004 | McDowell et al. |
| 6,887,247 B1 | 5/2005 | Couture et al. |
| 6,951,562 B2 | 10/2005 | Zwimmann |
| 6,981,976 B1 | 1/2006 | Schoenefeld |
| 7,033,363 B2 | 4/2006 | Powell |
| 7,141,074 B2 | 11/2006 | Fenger et al. |
| 7,163,542 B2 | 1/2007 | Ryan |
| 7,175,632 B2 | 2/2007 | Singhatat et al. |
| 7,189,242 B2 | 3/2007 | Boyd et al. |
| 7,210,881 B2 | 5/2007 | Greenberg |
| 7,299,561 B2 | 11/2007 | Castaneda |
| RE39,995 E | 1/2008 | Pepper et al. |
| 7,314,048 B2 | 1/2008 | Couture et al. |
| 7,442,197 B2 | 10/2008 | Abdelgany |
| 7,491,203 B2 | 2/2009 | Harris, Jr. et al. |
| 7,569,058 B2 | 8/2009 | Zwimmann |
| 7,588,577 B2 | 9/2009 | Fend et al. |
| 7,635,370 B2 | 12/2009 | Michelson |
| 7,752,771 B2 | 7/2010 | Wu |
| 7,753,914 B2 | 7/2010 | Ruhling et al. |
| 7,776,046 B2 | 8/2010 | Boyd |
| 7,862,567 B2 | 1/2011 | Schmieding |
| 7,927,332 B2 | 4/2011 | Huebner et al. |
| 8,012,157 B2 | 9/2011 | Chang et al. |
| 2002/0050463 A1 | 5/2002 | McDowell |
| 2003/0233098 A1 | 12/2003 | Vlarkworth |
| 2005/0085825 A1 | 4/2005 | Castaneda |
| 2005/0105983 A1 | 5/2005 | Hernandez |
| 2005/0147478 A1 | 7/2005 | Greenberg |
| 2005/0207856 A1 | 9/2005 | Inienhold |
| 2005/0222571 A1 | 10/2005 | Ryan |
| 2006/0149250 A1 | 7/2006 | Castaneda et al. |
| 2006/0184174 A1 | 8/2006 | Harris et al. |
| 2006/0190001 A1 | 8/2006 | Powell |
| 2007/0088364 A1 | 4/2007 | Ruhling et al. |
| 2007/0206996 A1 * | 9/2007 | Bharadwaj ......... A61B 17/1633 408/202 |
| 2008/0132904 A1 | 6/2008 | Usher et al. |
| 2009/0118742 A1 | 5/2009 | Hartmann et al. |
| 2009/0182344 A1 | 7/2009 | Harris, Jr. et al. |
| 2009/0204121 A1 | 8/2009 | Cavallazzi et al. |
| 2009/0234396 A1 | 9/2009 | Medoff |
| 2009/0275949 A1 | 11/2009 | Zwimmann |
| 2009/0306675 A1 | 12/2009 | Wong et al. |
| 2010/0069907 A1 | 3/2010 | Sidebotham et al. |
| 2011/0106086 A1 | 5/2011 | Laird |

* cited by examiner

DRILL GUIDE

CROSS-REFERENCE TO RELATED APPLICATIONS

This application is a divisional of U.S. application Ser. No. 13/545,377, filed Jul. 10, 2012, the disclosure of which is incorporated herein by reference.

BACKGROUND OF THE INVENTION

The present invention relates, in general, to a drill guide, and specifically to a drill guide having depth gauge features for controlling or gauging the depth to which a drill is inserted into bone.

Various bone drilling apparatus used, for example, to prepare a pilot hole(s) in bone for receiving a screw(s) or other fixation mechanism(s) are known. Such drilling apparatus, in some instances, may include a guide for receiving a drill bit and guiding the same into the bone to be treated. Further, the particular drill guide may also operate to limit the insertion depth of the drill bit. Examples of such drill guides are shown in U.S. Pat. Nos. 2,294,303, 6,699,253, and 7,163,542. These devices operate to, predominantly, prepare and/or initialize a hole in bone so that a screw or other fixation device may be easily inserted into the bone and through the hole.

Depth gauges for use in determining the depth to which a particular drill bit is inserted into bone are also known. An example of such a depth gauge is shown in U.S. Pat. No. 5,180,388, which discloses a depth gauge including a handle having a bore and adjacent sides with a scale for determining the insertion depth of a wire-type drill. In the '388 patent, bone pins may be inserted into corresponding pre-drilled holes formed via the wire-type drill. Other depth gauge-type devices are known in the art, which provide stop-mechanisms for controlling the maximum insertion depth of a drill bit into bone.

In some instances, however, it may be difficult to utilize the aforementioned drill guides or depth gauges with another device, such as a bone plate being secured to the surgical treatment site. In other words, the particular constructs noted above may not be amenable to engaging with an aperture in a bone plate or other surgical device, which is being secured to bone. Other deficiencies of such devices may include the general mode of operation thereof (e.g., such devices may be cumbersome to use, due to the multitude of parts comprising the device, etc.)

Accordingly, there exists a need for an improved drill guide and/or depth gauge, which overcomes the deficiencies of the prior art.

BRIEF SUMMARY OF THE INVENTION

A first embodiment of the present invention includes a drill guide for cooperating with and aligning a drill bit for drilling bone. In some cases, the drill guide may comprise a housing having a proximal section and a distal section, the housing defining a bore extending through the housing from the proximal section towards the distal section. A locking member may also be coupled with the housing, the locking member being adapted to engage and disengage with a locking portion of a drill bit, such that, when the locking member is engaged with the locking portion of the drill bit, the drill bit is locked within the bore in the housing along an axis of the bore extending between the proximal and distal sections, and, when the locking member is disengaged from the locking portion of the drill bit, the drill bit is movable within the bore along the axis.

Other aspects of the first embodiment may include a locking member that is fixedly connected to the proximal section of the housing. The locking member may also include internal threads adapted to engage with corresponding threads on the locking portion of the drill bit. The bore of the housing may also be dimensioned such that the locking portion of the drill bit is movable within the bore along the axis and distal to the locking member.

A second embodiment of the invention includes a drill guide for cooperating with and aligning a drill bit for drilling bone. In some cases, the drill guide may comprise a housing having a proximal section and a distal section, the housing defining a bore extending through the housing from the proximal section towards the distal section. A locking member may also be coupled with the housing, the locking member being adapted to engage with a locking portion of a drill bit to lock the drill bit within the bore of the housing along an axis of the bore extending between the proximal and distal sections. The drill guide may also include a movable guide disposed within the bore of the housing, the movable guide having a flange for engaging with a portion of a wall defining the bore of the housing, wherein the movable guide includes a bore extending therethrough and a surface adapted to engage with a surface on the drill bit, such that the movable guide is movable along the axis within the bore in the housing while the drill bit is moved along the axis.

The locking member, in some aspects of the second embodiment, may be adapted to disengage with the locking portion of the drill bit, such that the locking portion is movable within the bore in the housing to a position past the proximal section and the locking member and adjacent the distal section.

In a third embodiment of the present invention, a method of drilling bone is provided, such method comprising the steps of: (1) providing a drill guide having a housing with a proximal section and a distal section, the housing defining a bore extending through the housing from the proximal section towards the distal section; (2) inserting a distal portion of a drill bit within the bore in the housing; (3) engaging a locking section of the drill bit with a locking member coupled with the housing, such that the drill bit is locked within the bore in the housing along an axis of the bore extending between the proximal and distal sections; (4) disengaging the locking section of the drill bit from the locking member; and (5) moving the locking section of the drill bit within the bore in the housing and distally along the axis. While these steps are numbered above, no particular order is contemplated.

The steps of engaging and disengaging, in certain aspects of the third embodiment, may also include rotating the drill bit about the axis such that threads on the locking section of the drill bit engage or disengage, respectively, with internal threads on the locking member. Other aspects of the third embodiment may include the steps of: (1) engaging a surface on the drill bit with a surface on a movable guide disposed within the bore in the housing; and (2) moving the movable guide along the axis within the bore in the housing and towards the distal section by contacting the surface on the drill bit with the surface on the guide and simultaneously moving the drill bit distally.

BRIEF DESCRIPTION OF THE DRAWINGS

A more complete appreciation of the subject matter of the present invention and of the various advantages thereof can be realized by reference to the following detailed description in which reference is made to the accompanying drawings in which.

DETAILED DESCRIPTION

In describing particular embodiments of the present invention, specific terminology will be used for the sake of clarity. However, the invention is not intended to be limited to any specific terms used herein, and it is to be understood that each specific term includes all technical equivalents, which operate in a similar manner to accomplish a similar purpose.

Figure 1:
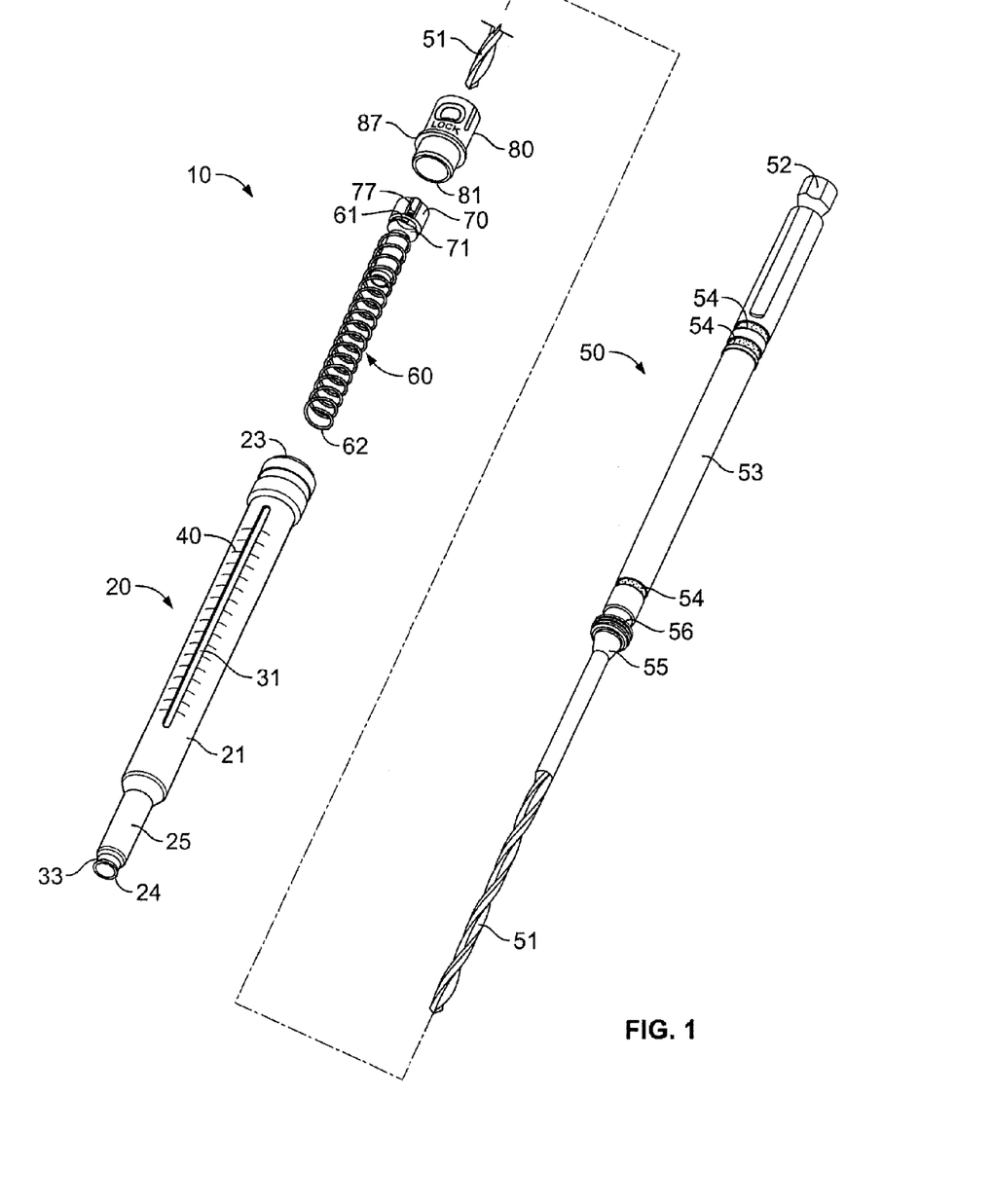
FIG. 1 is an exploded view of a drill guide and drill bit according to one embodiment of the present invention.

FIG. 1 depicts: (1) a drill guide 10 according to the present invention in which the guide 10 includes a guide tube 20 having depth gauge features or markings 40 thereon; and (2) a drill bit 50 insertable into and through the guide tube 20 for drilling bone. The drill guide 10 may function as a combination guide and depth gauge for simultaneously drilling a pilot hole(s) into bone and indicating the depth at which such hole(s) is drilled. In some instances, the drill guide 10 may be configured to interact with an aperture in a bone plate or other implantable device (hereinafter, "surgical device") to drill a corresponding pilot hole(s) for such aperture(s). A screw or other fixation mechanism may thereafter be inserted through the relevant aperture and into the pilot hole to secure the surgical device to the bone.

Figure 2A:
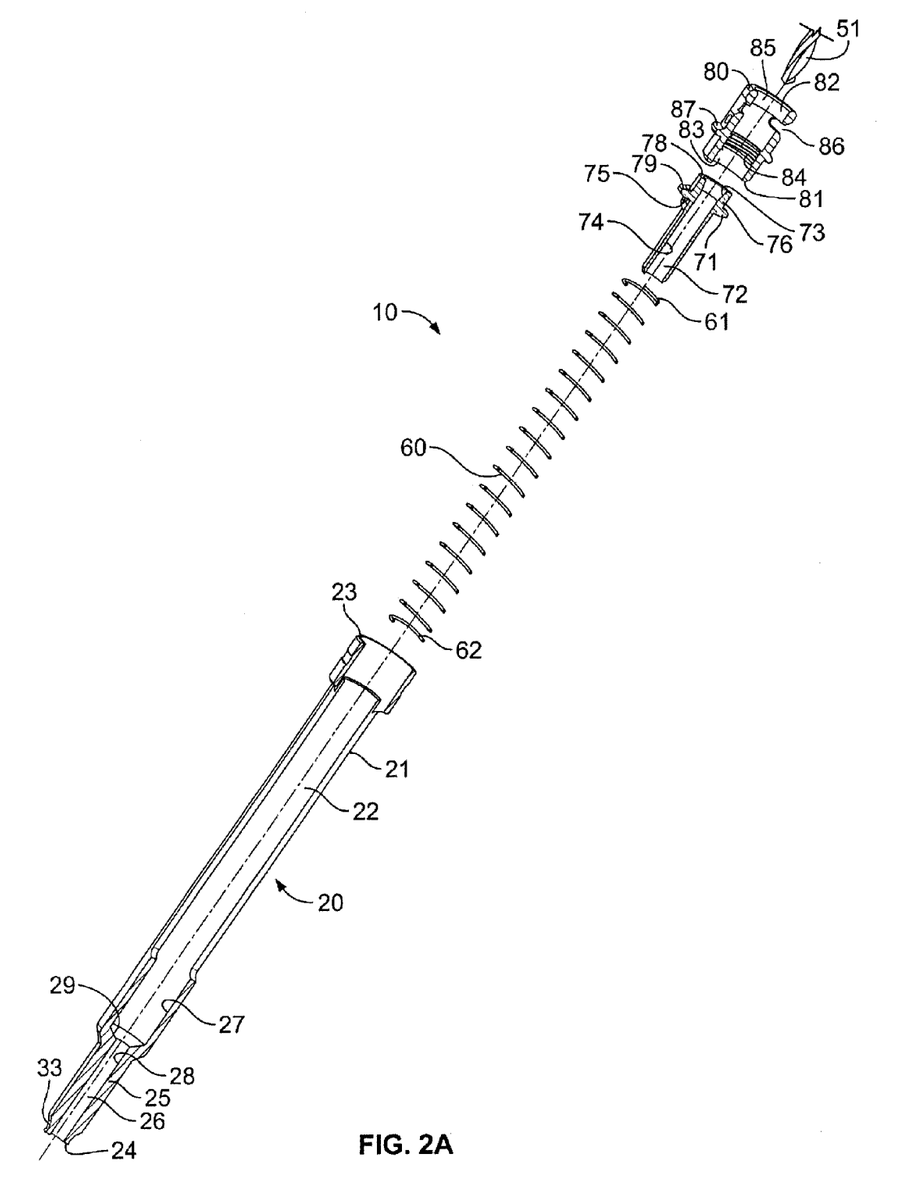
FIGS. 2A and 2B are cross-sectional views of the drill guide of FIG. 1, shown in assembled and exploded form, with the drill bit shown alongside the drill guide in FIG. 2B.
Figure 2B:
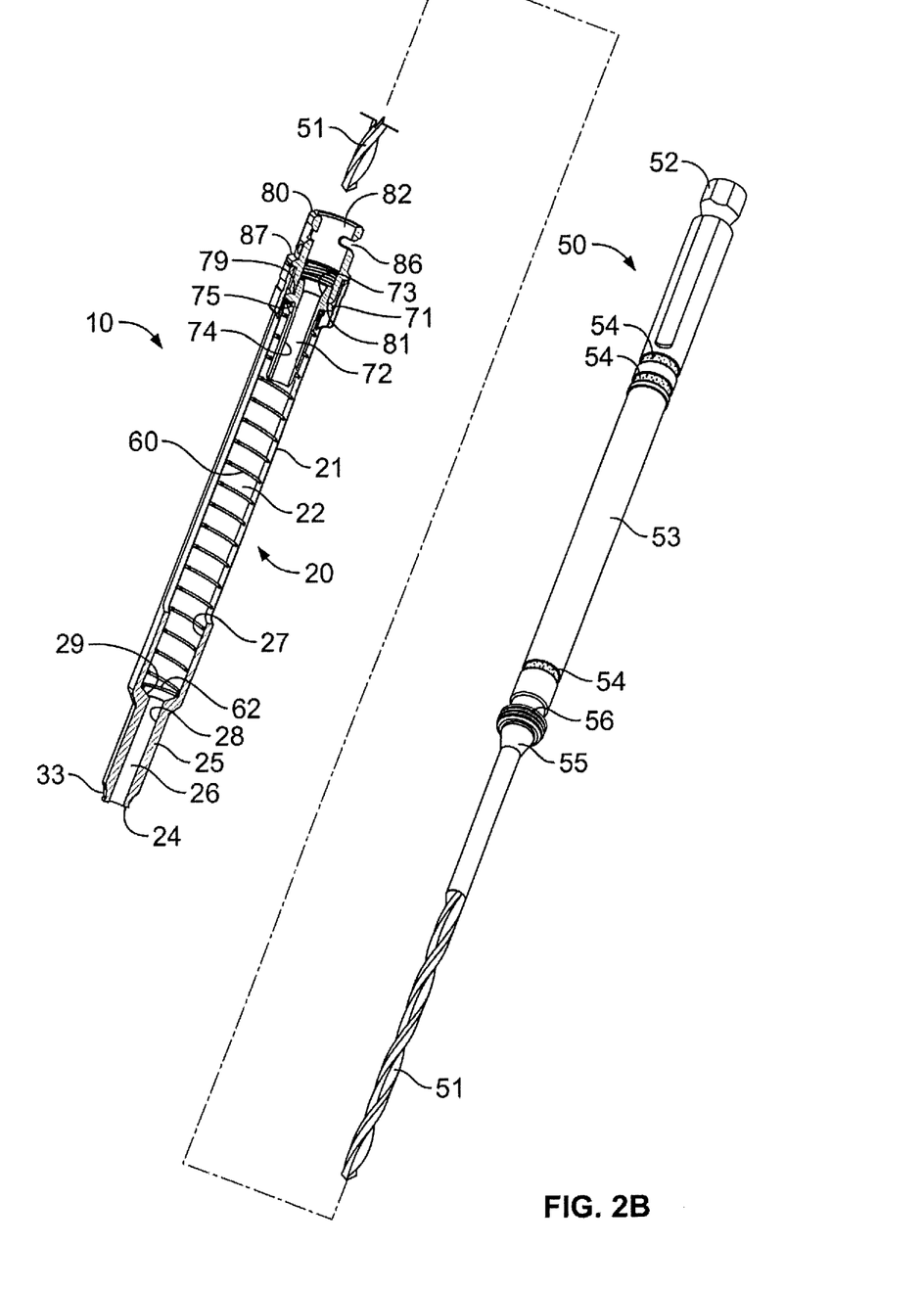

Referring to FIGS. 1 and 2A-2B, guide tube 20 of drill guide 10 may include an elongate cylindrical body 21 forming a main portion of the tube 20 and having a bore 22 running therethrough along an axis. The bore 22 may extend from a proximal end 23 to a distal end 24 of the tube 20; and, likewise, a slot 31 may be formed through the tube 20 and may extend, generally, between proximal 23 and distal 24 ends. The slot 31 may be used to view the drill bit 50 as it travels within bore 22. In one embodiment, particular indicia or a scale 40 may be positioned on body 21 adjacent slot 31 for determining the exact depth to which the drill bit 50 is inserted into bone.

Projecting from the main portion of guide tube 20 (i.e., cylindrical body 21) adjacent distal end 24 may be an extension 25 of the tube 20 formed integral therewith or as a separate component part. Extension 25 may, in one embodiment, be generally cylindrical in shape and may have a chamfered section 33 on an external surface thereof for engaging with an aperture formed in a surgical device. Extension 25 also, like guide tube 20, has a bore 26 running therethrough. Thus, the combination of bore 22 through tube 20 and bore 26 through extension 25 allows the drill bit 50 to be inserted completely through drill guide 10. In a particular embodiment, bore 22 of tube 20 may form a first relatively wider section 27, and bore 26 of extension 25 may define a second relatively narrower section 28 (e.g., in terms of diameter) defining a stop surface 29 therebetween. In some embodiments, second section 28 defined by bore 26 may closely approximate the size and shape of a portion of drill bit 50 so as to serve as a guide and stabilize the bit 50 when inserted into bone. Stated differently, as second section 28 defined by bore 26 may closely approximate the size and shape of a portion of drill bit 50, such section 28 may act as a longitudinal guide stabilizing drill bit 50 as it is inserted into bone. Stop surface 29 between first 27 and second 28 sections may also serve to limit the insertion depth of the drill bit 50, as will be described in more detail below.

Housed within bore 22 of tube 20 may also be a spring 60, as shown in detail in FIGS. 2A-2B. Spring 60 may be a conventional helical spring, although other spring types are contemplated; and such spring 60 may extend, in its expanded state, along the entirety of bore 22 of tube 20. A distal end 62 of spring 60 may also abut stop surface 29 so as to allow spring 60 to be compressed within bore 22, when desired.

A movable guide 70 may also form part of drill guide 10, such guide 70 being shown in detail in both FIGS. 1 and 2A-2B. Guide 70 may generally be configured to be situated within bore 22 of tube 20, such that a radial flange 71 extending from the guide 70 may ride along an interior surface of bore 22 (FIGS. 2A-2B). Guide 70 has a bore 72 extending therethrough, such bore 72 having a first tapered section 73 and a second generally straight section 74. Second straight section 74 of bore 72 may be configured to receive and interact with a portion of drill bit 50, while first tapered section 73 may be configured to interact with a separate section of drill bit 50, described in more detail below. Radially extending flange 71 of guide 70, and specifically a bottom surface 75 thereof, may also be configured to interact with a proximal end 61 of spring 60 to compress spring 60 in bore 22 of tube 20, as shown best in FIGS. 2A-B and FIG. 4. A protrusion 77, shown in FIGS. 1 and 3, may also extend from a surface of the guide 70 for interacting with the slot 31 or another channel in tube 20, and thereby maintaining and/or aligning movable guide 70 appropriately as it travels along bore 22 of tube 20 (e.g., during drilling)

Referring again to FIG. 2A-2B, a top surface 79 of radially extending flange 71 may interact with a cap 80 inserted into the proximal end 23 of guide tube 20. In one embodiment, cap 80 may include external threading (not shown), which interacts with internal threading (not shown) formed on an interior surface of tube 20 adjacent proximal end 23. Thus, cap 80 may be screwed into engagement with tube 20. Once cap 80 is secured within tube 20 as such, top surface 79 of flange 71 may interact with a distal end 81 or other surface of cap 80 thereby preventing movable guide 70 from being pushed out of bore 22 in tube 20 via spring 60. In other words, movable guide 70 may be compressed between spring 60 and distal end 81 of cap 80, thereby retaining guide 70 in tube 20. Accordingly, via the interaction between cap 80 and movable guide 70, spring 60 may remain compressed (to some minor degree) at all times.

In one embodiment, cap 80 may include a bore 82 therethrough with multiple sections, one such section being a distal section 83 having a diameter that is sized to receive a proximal section 76 of movable guide 70. Proximal section 76 of movable guide 70 may, therefore, be disposed within distal section 83 of bore 82 in cap 80, and flange 71 of guide 70 may interact with distal end 81 of cap 80. A second intermediate section 84 of bore 82 may be situated above distal section 83, and may neck-down creating a reduced diameter section. Such section 84 of bore 82 may optionally include threading to interact with corresponding threading formed on a section of drill bit 50. Depending on the dimensions of moveable guide 70, intermediate section 84 of bore 82, via the difference in diameter between distal section 83 and intermediate section 84, may define a stop surface that contacts a proximal end 78 of movable guide 70 to assist in retaining the same within tube 20. A final proximal section 85 of bore 82 through cap 80 may be sized similar to distal section 83, thus defining a step between intermediate 84 and proximal 85 sections of bore 82. One or more apertures 86 may also be disposed through cap 80 nearing proximal section 85 of bore 82 to allow a surgeon, nurse, or other skilled practitioner (hereinafter, "the user") to view a portion of the drill bit 50 as it is inserted through drill guide 10. A flange 87 may also be arranged on cap 80 for abutting against a portion of tube 20 to thereby limit the insertion of cap 80 within bore 22 of tube 20.

Referring again to FIG. 1, there is shown a drill bit 50 having a cutting section 51, a tool engaging section 52 (e.g., for connecting to a power tool-type device), and a shaft 53 running therebetween. Shaft 53 may have a series of markers 54 thereon for determining a depth to which the drill bit 50 is inserted into bone (i.e., by aligning with a feature of the drill guide 10), and/or for determining whether the drill bit 50 is in a locked or unlocked orientation, as described more fully below. Drill bit 50 may also include a tapered section 55 and a flange 56 adjacent the tapered section 55. In one embodiment, flange 56 may include external threading thereon that may interact with the internal threading on intermediate section 84 of bore 82 through cap 80. Drill bit 50 may, in one embodiment, be generally cylindrical in shape, and may be sized for insertion through cap 80 and guide tube 20 (including extension 25) of drill guide 10.

To assemble drill guide 10, as shown in detail in FIG. 1, a user may first insert movable guide 70, and specifically second section 74 thereof, into the proximal portion 61 of spring 60, such that flange 71 of guide 70 engages a portion of spring 60. Then, the movable guide 70 and spring 60 construct may be inserted within bore 22 of guide tube 20 so that a distal end 62 of spring 60 may abut stop surface 29. With these components assembled in the manner described, a user may then insert distal end 81 of cap 80 into proximal end 23 of tube 20 and screw cap 80 into tube 20 until such a point as: (1) flange 87 of cap 80 abuts proximal end 23 of tube 20; (2) intermediate section 84 of bore 82 abuts proximal end 78 of movable guide 70; and/or (3) distal end 81 of cap 80 abuts flange 71 of guide 70. In this configuration, movable guide 70 may move longitudinally along and within bore 22 of guide tube 20 to interact with drill bit 50 during drilling of bone. To be exact, since flange 71 of movable guide 70 contacts a portion of spring 60, and a distal end 62 of spring 60 abuts stop surface 29, such spring 60 may be compressed as guide 70 is moved axially within bore 22 of guide tube 20. In other embodiments, drill guide 10 may be manufactured such that cap 80 is integral with tube 20, creating a single monolithic structure in which moveable guide 70 and spring 60 are disposed.

With the components of drill guide 10 assembled, drill bit 50 may be inserted within and through drill guide 10 (e.g., for drilling) as follows. Cutting section 51 of drill bit 50 may first be inserted through bore 82 in cap 80, bore 72 in movable guide 70, and partway through bore 22 in guide tube 20. During this insertion, drill bit 50 may be advanced until such a point as flange 56 of bit 50 engages or abuts intermediate section 84 of bore 82 in cap 80. Since flange 56 may include external threading thereon, which may interact with the internal threading on intermediate section 84 of bore 82, flange 56, and thus drill bit 50, may initially be precluded from traveling through intermediate section 84 of bore 82 of cap 80 (e.g., since the threading on intermediate section 84 may prevent movement of drill bit 50 distally without rotation thereof). Subsequently, a user may elect to rotate drill bit 50 about its longitudinal axis to screw flange 56 into engagement with intermediate section 84 of bore 82. In this condition, i.e., during engagement of flange 56 with intermediate section 84, drill bit 50 may be locked in position in an axial direction within bore 22, such that drill bit cannot travel along the axis of bore 22 without rotating drill bit 50 about the axis. Such a locked configuration may be displayed to a user through the alignment of an indicator 54 on drill bit 50 with one or more apertures 86 in cap 80, as shown in detail in FIG. 3. In particular, a specific reference marker 54 on drill bit 50 may be viewable through the one or more apertures 86 in cap 80 only when the drill bit 50 is situated in the locked condition. A user may therefore be informed as to when the drill bit 50 is disposed in the locked configuration and when it is not.

With flange 56 screwed into engagement with intermediate section 84 of bore 82 of cap 80, drill bit 50 may act as a manipulation tool for manipulating drill guide 10 (e.g., since drill bit 50 is locked to drill guide 10). As such, it is possible for a user to manipulate drill guide 10 via drill bit 50 and engage chamfered section 33 of extension 25 with an aperture in a surgical device (not shown) without fear of disconnection between drill bit 50 and drill guide 10. That is, drill bit 50 may first be connected with a drill, and drill guide 10 may thereafter be engaged with drill bit 50, such that the two are essentially locked together. This would allow a user to perform the step of engaging chamfered section 33 of extension 25 with an aperture in a surgical device (not shown) and then to drill directly afterward without having to align the drill bit 50 into the engaged drill guide 10.

Once chamfered section 33 of guide tube 20 is engaged to an appropriate aperture in a surgical device, a user may then continue to rotate drill bit 50 about its longitudinal axis to cause the threading on flange 56 to disengage with the corresponding threading on intermediate section 84 of bore 82 through cap 80. In this condition, as shown in detail in FIG. 4, flange 56 of drill bit 50 may be engaged with proximal end 78 of movable guide 70, and/or tapered section 55 of drill bit 50 may be engaged with tapered section 73 of bore 72 through guide 70. Accordingly, movement of drill bit 50 in an axial direction may cause corresponding movement of movable guide 70 within bore 22 of guide tube 20. Additionally, as flange 71 of movable guide 70 may be engaged with spring 60, there may be some resistance to such movement, thereby providing a user with a tactile sensation that the drill bit 50 is smoothly gliding through drill guide 10. Such resistance may also keep movable guide 70 disposed against tapered section 55 and flange 56 of drill bit 50.

During movement of drill bit 50 through guide tube 20 via movable guide 70, as discussed above, a user may also view the depth gauge features or markings 40 on tube 20 in conjunction with a particular reference marker 54 on drill bit 50, which indicates the depth at which bit 50 is inserted into bone. Stated differently, as drill bit 50 is moved longitudinally or axially through guide tube 20, a user may view a particular reference marker 54 on such bit 50 through slot 31 in tube 20, and the position of such marker 54 in relation to the depth gauge markings 40 on tube 20 may indicate the depth at which drill bit 50 is inserted into bone. The same function may be provided by viewing protrusion 77 on movable guide 70 through slot 31. For instance, a user may view the aforementioned reference marker 54 (or protrusion 77) traveling from a marking 40 on guide tube 20 reading zero (0) millimeters to a marking 40 reading twenty (20) millimeters and thereby know that the drill bit 50 has been inserted twenty (20) millimeters into bone. During such axial movement of drill bit 50, movable guide 70 may also be stabilized within bore 22 of guide tube 20 via the interaction between protrusion 77 on guide 70 and slot 31 formed through tube 20 (e.g., such guide 70 may be restricted from unwanted rotation within tube 20 as drill bit 50 is rotated for drilling) Thus, in some instances, protrusion 77 may serve a dual function.

Figure 4:
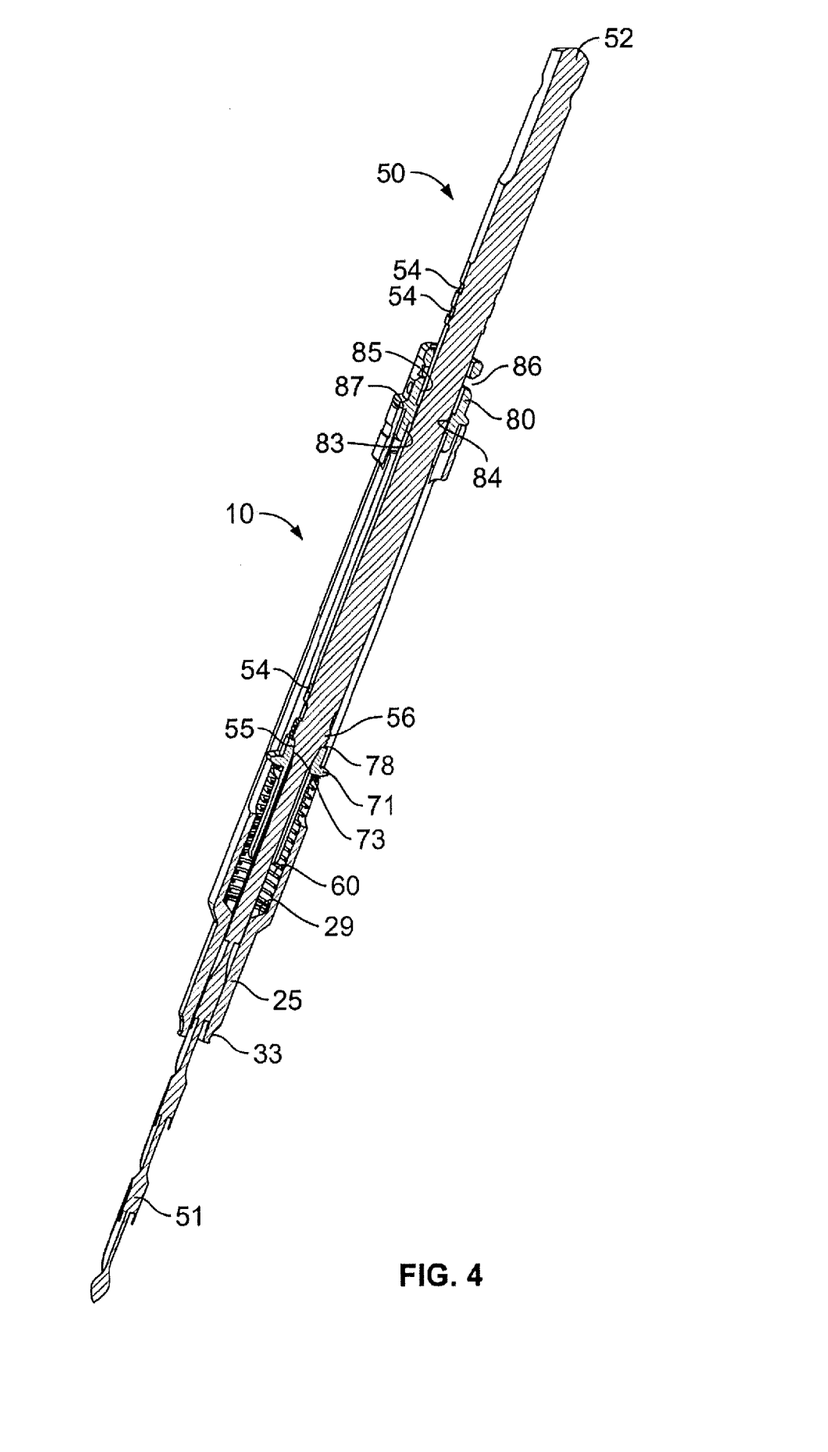
FIG. 4 is a cross section of the drill guide of FIG. 1 with the drill bit inserted therein and in an unlocked position.

Referring still to FIG. 4, upon moving drill bit 50 (and thus movable guide 70) a sufficient distance in the distal direction, protrusion 77 on movable guide 70 may engage with a portion of slot 31 in guide tube 20, thereby preventing further movement of drill bit 50 distally. Thus, such portion of slot 31 may act as a depth-limiting feature of drill guide 10 for limiting the maximum depth to which the drill bit 50 may be inserted into bone; although, as noted above, it is also contemplated that a user may simply stop drilling when the desired depth for drilling has been reached.

It is notable that, in the unlocked condition described above, the reference marker 54 on drill bit 50 indicating that such bit 50 is in a locked condition will no longer be viewable through apertures 86 in cap 80. Thus, a user is informed that drill bit 50 is in the unlocked state and is freely movable within bore 22 in guide tube 20 once flange 56 on drill bit 50 is disengaged from intermediate section 84 of bore 82 through cap 80.

With the initial pilot hole drilled according to the above-described method, a user may then disengage chamfered section 33 of extension 25 from the aperture in the surgical device and continue to drill another pilot hole(s) utilizing a different aperture(s) in the surgical device. This process may be repeated, as necessary, until all pilot holes are drilled. Subsequently, the user may insert a fixation mechanism (not shown), such as, for example, a bone screw or fixation pin through the aperture in the surgical device and into the corresponding pilot hole. The surgical device may then be secured to bone via the fixation mechanism(s) inserted into the pilot hole(s).

Figure 3:
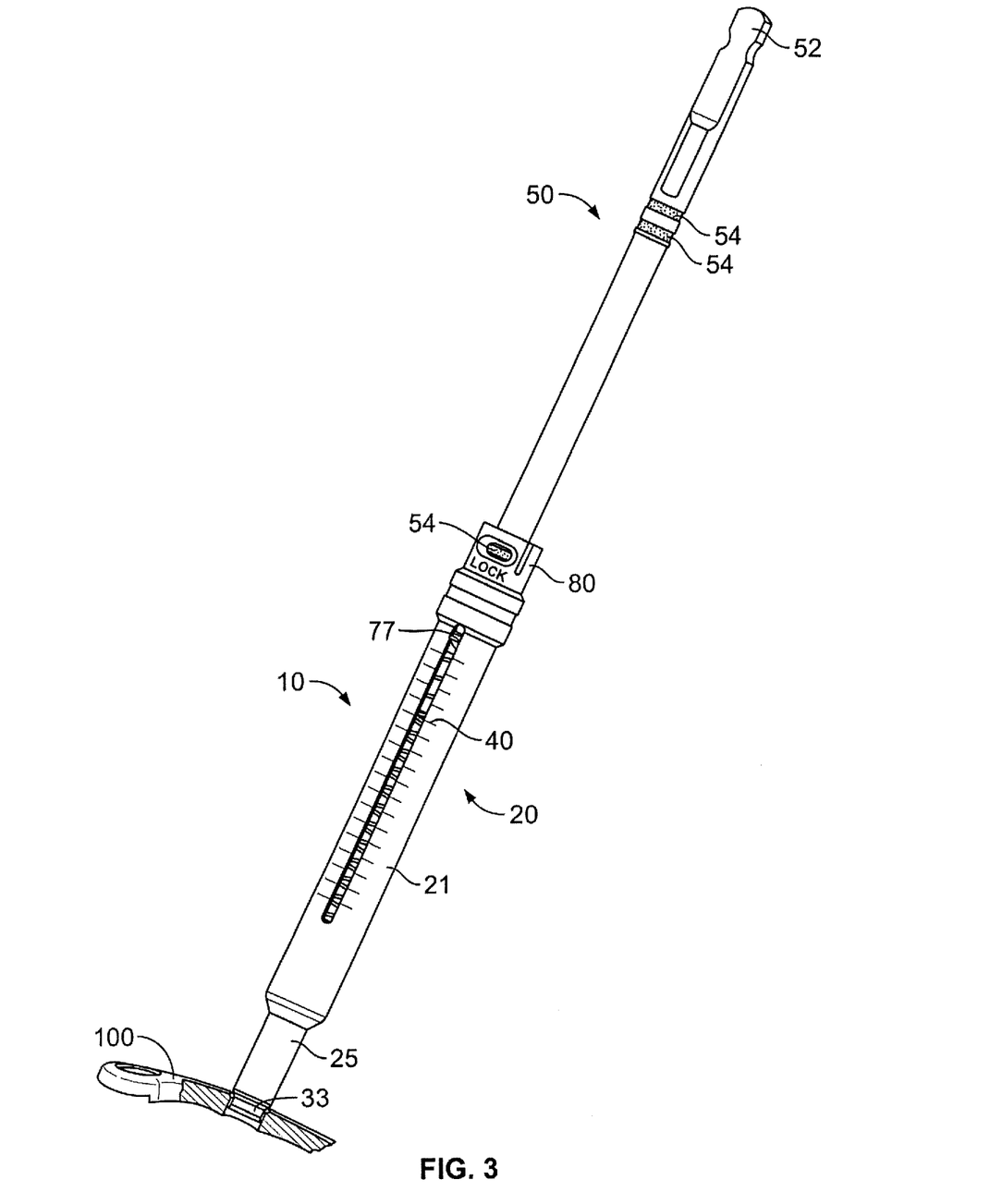
FIG. 3 is a perspective view of the drill guide of FIG. 1 with the drill bit inserted therein and in a locked position.

In one embodiment, to remove drill guide 10 from engagement with the surgical device, a user may simply retract drill bit 50 proximally until such a point as flange 56 abuts intermediate section 84 of bore 82 through cap 80. The user may then rotate drill bit 50 so that the threading on flange 56 reengages with the threading on intermediate section 84 of bore 82. This places drill bit 50 back into its locked state, which may be conveyed to a user via a reference marker 54 on drill bit 50, which is viewable through aperture(s) 86 in cap 80 (FIG. 3). With drill bit 50 in its locked state, a user may then simply remove the drill bit 50/drill guide 10 construct (e.g., as one piece) from contact with the surgical device. Thereafter, the user may elect to continue to rotate the drill bit 50, such that flange 56 disengages with intermediate section 84 of bore 82 and drill bit 50 is removed or separated from drill guide 10. The drilling process, at this stage, may be complete, and a user may elect to utilize the drill guide 10 and drill bit 50 in another surgical procedure, if desired.

In the devices depicted in the figures, particular structures are shown that are adapted to provide an improved drilling apparatus and/or allow for an improved method of drilling bone. The invention also contemplates the use of any alternative structures for such purposes, including structures having different lengths, shapes, and/or configurations. For example, although drill guide 10 has been described as engaging an aperture in a surgical device, it is equally contemplated that a portion of drill guide 10 (e.g., chamfered section 33) may be configured to interact directly with bone. In this embodiment, chamfered section 33 may include teeth or other such serrations so that, once engaged with bone, drill guide 10 may be stabilized with respect thereto. In this condition, drilling would take place as described above, except that drill guide 10 would directly contact bone instead of contacting an intermediate surgical device (e.g., a bone plate aperture, etc.) It is also contemplated that the aforementioned teeth or serrations may be included on chamfered section 33, and such section 33 may simultaneously engage an intermediate surgical device and bone during drilling As another example, while drill bit 50 may be locked axially with respect to drill guide 10 through interaction of threading on the drill bit 50 with threading on a portion of guide 10, other locking mechanisms are contemplated. For instance, a portion of drill bit 50 may be designed to be press-fit into a portion of cap 80 (or another portion of guide 10), such that drill bit 50 is lockable in an axial direction within bore 22. In other words, slight differences in dimensions between one section of drill bit 50 and a corresponding section of cap 80 (or another section of guide 10) may cause drill bit 50 to become fixed within cap 80 (or the other section of guide 10) when such sections interact. Subsequently, upon application of sufficient force, drill bit 50 may be driven through the "press-fit" region, through the remainder of drill guide 10, and into bone. Thus, with this mechanism, drill bit 50 may be provisionally locked within bore 22 in an axial direction.

In another example of this type of "press-fit" configuration, an outwardly extending flange on drill bit 50 may interact with two inwardly extending flanges on cap 80 (or guide 10). The outwardly extending flange may be dimensioned to create a slight dimensional interference with each of the inwardly extending flanges. Between the inwardly extending flanges may be an annular recess. The outwardly extending flange of drill bit 50 may pressed to pass the initial inwardly extending flange with a force that overcomes the dimensional interference and allows the outwardly extending flange to be temporarily retained within the annular recess, thereby locking the drill bit 50 to the drill guide 10 in a manner similar to that described above.

A protrusion and detent mechanism may also be used in place of the aforementioned locking structures. For example, a protrusion on drill bit 50 may selectively engage with a corresponding detent in cap 80 (or another portion of guide 10) so as to provisionally lock drill bit 50 axially within bore 22 of tube 20. After such engagement, a user may then cause the protrusion on drill bit 50 to disengage with the detent in cap 80 (or other portion of guide 10) to allow drill bit 50 to move within bore 22 in tube 20 and into bone. Likewise, it is also contemplated that cap 80 (or the other portion of guide 10) may contain the protrusion and drill 50 the detent. It is therefore apparent that other locking mechanisms beyond that disclosed in the main embodiment may be used.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will also be appreciated that the various dependent claims and the features set forth therein can be combined in different ways than presented in the initial claims. It will also be appreciated that the features described in connection with individual embodiments may be shared with others of the described embodiments.

The invention claimed is:

1. A method of drilling bone comprising:
providing a drill guide having a housing with a proximal section and a distal section, the housing defining a bore extending through the housing from the proximal section towards the distal section;
inserting a distal portion of a drill bit within the bore in the housing;
engaging a locking section of the drill bit with a locking member coupled with the housing, such that the drill bit is locked within the bore in the housing to prevent relative axial movement of the drill bit with respect to the housing along an axis of the bore extending between the proximal and distal sections;
disengaging the locking section of the drill bit from the locking member by moving the locking section of the drill bit within the bore in the housing and distally along the axis of the bore past the locking member to allow free relative axial and rotational movement of the drill bit with respect to the housing along the axis of the bore; and
drilling into bone with the drill bit after the step of disengaging.

2. The method of claim 1, further comprising steps of:
engaging a surface on the drill bit with a surface on a movable guide disposed within the bore in the housing; and
moving the movable guide along the axis within the bore in the housing and towards the distal section by contacting the surface on the drill bit with the surface on the guide and simultaneously moving the drill bit distally.

3. The method of claim 2, wherein the movable guide includes a bore and the method further comprises a step of inserting the distal portion of the drill bit through the bore of the movable guide.

4. The method of claim 3, wherein the movable guide includes a flange extending from the guide for engaging with a portion of a wall defining the bore of the housing.

5. The method of claim 1, further comprising a step of drilling the bone using the drill bit to form a pilot hole for receiving a fixation mechanism therein.

6. The method of claim 1, further comprising a step of viewing indicia on a surface of the housing while the locking section of the drill bit is moved within the bore in the housing to determine the depth at which the drill bit is inserted into bone.

7. The method of claim 1, wherein the steps of engaging and disengaging include rotating the drill bit about the axis such that threads on the locking section of the drill bit engage or disengage, respectively, with internal threads on the locking member.

8. A method of drilling bone comprising:
providing a drill guide having a housing with a proximal section and a distal section, the housing defining a bore extending through the housing from the proximal section towards the distal section;
inserting a distal portion of a drill bit having a cutting section within the bore in the housing;
engaging a locking section of the drill bit with a locking member coupled with the housing, such that the drill bit is locked within the bore in the housing to prevent relative axial movement of the drill bit with respect to the housing along an axis of the bore extending between the proximal and distal sections;
disengaging the locking section of the drill bit from the locking member to allow free relative axial movement of the drill bit with respect to the housing along the axis of the bore;
engaging a surface on the drill bit with a surface on a movable guide disposed within the bore in the housing;
moving the locking section of the drill bit within the bore in the housing and distally along the axis;
moving the movable guide along the axis within the bore in the housing and towards the distal section by contacting the surface on the drill bit with the surface on the guide and simultaneously moving the drill bit distally; and
drilling into bone with the drill bit,
wherein a projection extending from the moveable guide engages with a slot formed in the housing to prevent rotation of the movable guide relative to the housing.

9. The method of claim 8, wherein the movable guide includes a bore and the method further comprises a step of inserting the distal portion of the drill bit through the bore of the movable guide.

10. The method of claim 9, wherein the movable guide includes a flange extending from the guide for engaging with a portion of a wall defining the bore of the housing.

11. The method of claim 8, wherein the step of drilling into bone with the drill bit forms a pilot hole for receiving a fixation mechanism therein.

12. The method of claim 8, further comprising a step of viewing indicia on a surface of the housing while the locking section of the drill bit is moved within the bore in the housing to determine the depth at which the drill bit is inserted into bone.

13. The method of claim 8, wherein the steps of engaging and disengaging include rotating the drill bit about the axis such that threads on the locking section of the drill bit engage or disengage, respectively, with internal threads on the locking member.

* * * * *